(12) United States Patent
Lee et al.

(10) Patent No.: US 11,444,327 B2
(45) Date of Patent: Sep. 13, 2022

(54) ELECTROLYTE SOLUTION FOR LITHIUM SECONDARY BATTERIES AND LITHIUM SECONDARY BATTERY INCLUDING THE SAME

(71) Applicants: Hyundai Motor Company, Seoul (KR); Kia Motors Corporation, Seoul (KR)

(72) Inventors: Yoon Sung Lee, Gyeonggi-do (KR); Ik Kyu Kim, Gyeonggi-do (KR); Seung Min Oh, Incheon (KR); Young Woo Lee, Gyeonggi-do (KR); Dong Jun Kim, Gyeonggi-do (KR); Sung Ho Ban, Gyeonggi-do (KR); Sung Hoon Lim, Gyeonggi-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 275 days.

(21) Appl. No.: 16/897,916

(22) Filed: Jun. 10, 2020

(65) Prior Publication Data

US 2021/0184262 A1 Jun. 17, 2021

(30) Foreign Application Priority Data

Dec. 13, 2019 (KR) .................. 10-2019-0167251

(51) Int. Cl.
| | |
|---|---|
| *H01M 10/0567* | (2010.01) |
| *H01M 10/0568* | (2010.01) |
| *H01M 10/0569* | (2010.01) |
| *H01M 10/0525* | (2010.01) |
| *H01M 4/505* | (2010.01) |
| *H01M 4/525* | (2010.01) |

(Continued)

(52) U.S. Cl.
CPC ....... *H01M 10/0567* (2013.01); *C07C 205/57* (2013.01); *H01M 4/505* (2013.01); *H01M 4/525* (2013.01); *H01M 4/587* (2013.01); *H01M 10/0525* (2013.01); *H01M 10/0568* (2013.01); *H01M 10/0569* (2013.01); *H01M 2220/20* (2013.01); *H01M 2300/0025* (2013.01)

(58) Field of Classification Search
None
See application file for complete search history.

(56) References Cited

U.S. PATENT DOCUMENTS 9,466,857 B1 * 10/2016 Cheng ............... H01M 10/0569

FOREIGN PATENT DOCUMENTS

| JP | H1131526 A | 2/1999 |
|---|---|---|
| KR | 2019-0092149 A | 8/2019 |
| WO | 2020/170833 A1 | 8/2020 |

OTHER PUBLICATIONS

Allart et al., "A Stable Bis-Allyloxycarbonyl Biotin Aldehyde Derivative for Biotinylation via Reductive Alkylation: Application to the Synthesis of a Biotinylated Doxorubicin Derivative", Bioconjugate Chemistry, Nov. 20, 2002, 14(1):187-194.

* cited by examiner

*Primary Examiner* — Christopher P Domone
(74) *Attorney, Agent, or Firm* — Fox Rothschild LLP

(57) ABSTRACT

Disclosed are an electrolyte solution for lithium secondary batteries capable of increasing the lifetime of the lithium secondary batteries and a lithium secondary battery including the same. Provided is an electrolyte solution for lithium secondary batteries including a lithium salt, a solvent and allyl(4-nitrophenyl) carbonate.

10 Claims, 3 Drawing Sheets

(51) Int. Cl.
*H01M 4/587* (2010.01)
*C07C 205/57* (2006.01)

ELECTROLYTE SOLUTION FOR LITHIUM SECONDARY BATTERIES AND LITHIUM SECONDARY BATTERY INCLUDING THE SAME

CROSS-REFERENCE TO RELATED APPLICATION

This application claims the priority benefit of Korean Patent Application No. 10-2019-0167251, filed on Dec. 13, 2019 in the Korean Intellectual Property Office, the disclosure of which is incorporated herein by reference.

TECHNICAL FIELD

The present invention relates to an electrolyte solution for lithium secondary batteries and a lithium secondary battery including the same. Particularly, the electrolyte solution for lithium secondary batteries may increase the lifetime of the lithium secondary batteries.

BACKGROUND OF THE INVENTION

A lithium secondary battery is an energy storage device that includes a positive electrode for supplying lithium and a negative electrode for receiving lithium during charging, an electrolyte serving as a medium for transferring a lithium ion, and a separator for separating the positive electrode and the negative electrode from each other. The lithium secondary battery generates electrical energy and stores the same through a change in chemical potential when the lithium ion is intercalated or de-intercalated on the positive electrode or the negative electrode.

Such a lithium secondary battery has mainly been used in portable electronic devices, but has recently come to be used as energy storage means for electric vehicles (EVs) and hybrid electric vehicles (HEVs) in response to recent commercialization of electric vehicles (EVs) and hybrid electric vehicles (HEVs).

Meanwhile, research on increasing the energy density of the lithium secondary battery has been conducted in order to increase the driving distance of electric vehicles, and increasing the energy density of lithium secondary batteries is possible by increasing the capacity of the positive electrode.

The increase in the capacity of the positive electrode can be achieved through Ni enrichment, which is a method of increasing the Ni content of Ni—Co—Mn-based oxide constituting a positive-electrode active material, or can be achieved by increasing the positive-electrode charging voltage.

However, Ni-enriched Ni—Co—Mn-based oxides have high interfacial reactivity and an unstable crystal structure, disadvantageously accelerating deterioration during cycles and making it difficult to secure long-life performance.

The above information disclosed in this Background section is provided only for enhancement of understanding of the background of the invention and therefore it may contain information that does not form the prior art that is already known in this country to a person of ordinary skill in the art.

SUMMARY OF THE INVENTION

In preferred aspects, provided are, inter alfa, an electrolyte solution for lithium secondary batteries capable of increasing the lifetime of the lithium secondary batteries and a lithium secondary battery including the electrolyte.

In an aspect, provided is an electrolyte solution for lithium secondary batteries including a lithium salt, a solvent and allyl(4-nitrophenyl) carbonate represented by the following Formula 1.

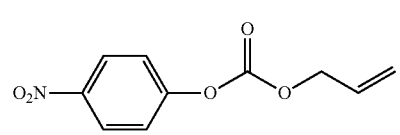

[Formula 1]

The electrolyte solution may suitably include the allyl(4-nitrophenyl) carbonate in an amount of about 3.0% by weight or less with respect to the total weight of the electrolyte solution.

Preferably, the electrolyte solution may include the allyl (4-nitrophenyl) carbonate in an amount of about 0.5 to 2.0% by weight with respect to the total weight of the electrolyte solution.

The lithium salt may suitably include one o more selected from the group consisting of $LiPF_6$, $LiBF_4$, $LiClO_4$, $LiCl$, $LiBr$, $LiI$, $LiB_{10}Cl_{10}$, $LiCF_3SO_3$, $LiCF_3CO_2$, $LiAsF_6$, $LiSbF_6$, $LiAlCl_4$, $CH_3SO_3Li$, $CF_3SO_3Li$, $LiN(SO_2C_2F_5)_2$, $Li(CF_3SO_2)_2N$, $LiC_4F_9SO_3$, $LiB(C_6H_5)_4$, $Li(SO_2F)_2N$ (LiFSI) and $(CF_3SO_2)_2NLi$.

The solvent may suitably include one or more selected from the group consisting of carbonate solvents, ester solvents, ether solvents and ketone solvents.

The electrolyte solution for lithium secondary batteries may further include a positive-electrode additive, wherein the positive-electrode additive is $LiPO_2F_2$.

In another aspect, provided is a lithium secondary battery including the electrolyte solution described above. In addition, the lithium secondary battery may further include a positive electrode including a positive-electrode active material containing Ni, Co and Mn, a negative electrode including a carbon (C)-based negative-electrode active material, and a separator interposed between the positive electrode and the negative electrode.

The lithium secondary battery may be a discharge retention of about 94% or greater, measured after 200 cycles, each cycle including 0.5 C cc/cv charging and 0.5 C cc/cv discharging at 2.5 to 4.2V (cut-off) and at a temperature of 45° C.

Vehicles are also provided that comprise a lithium secondary battery as disclosed herein.

Other aspects of the invention are disclosed infra.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Figure 1:
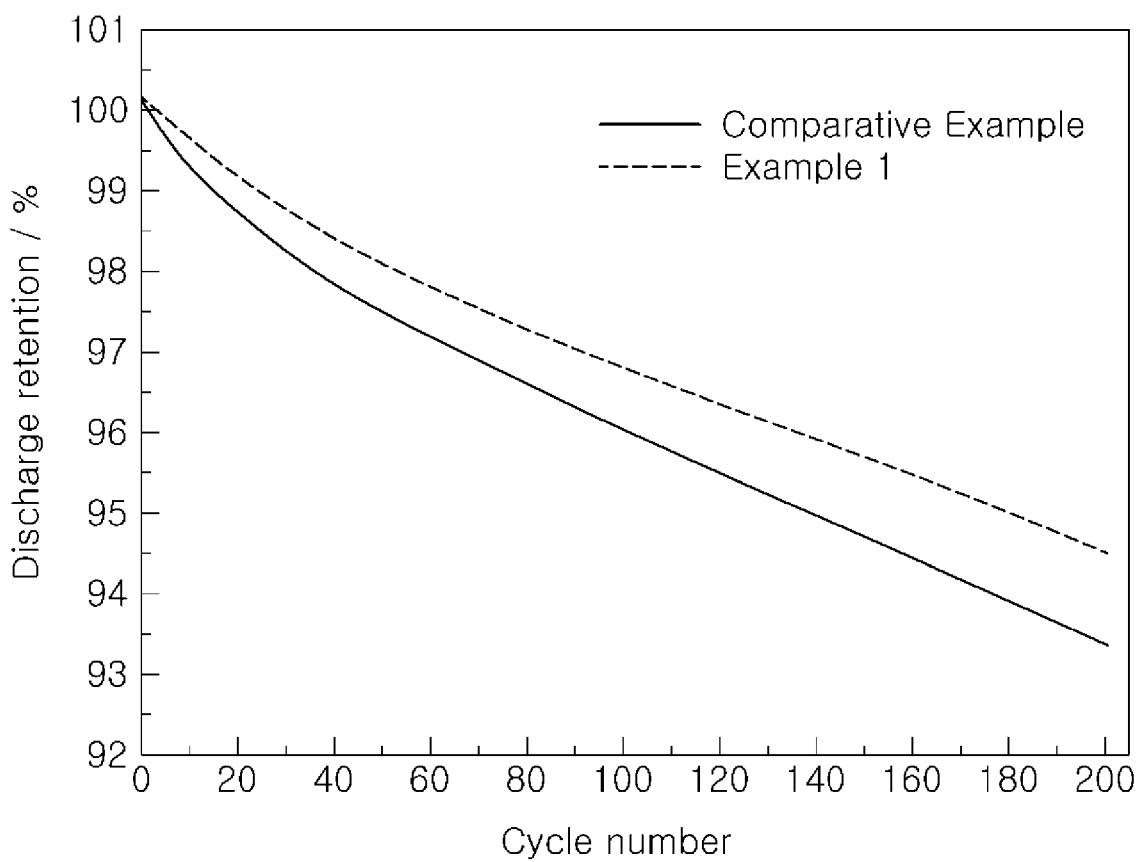
FIG. 1 is a graph showing the evaluation results of characteristics after addition of additives in Experiment 1 according to an exemplary embodiment of the present invention.

Reference will now be made in detail to the preferred embodiments of the present invention, examples of which are illustrated in the accompanying drawings. However, the present invention is not limited to the embodiments, and may be implemented in various forms. The embodiments are provided only to fully illustrate the present invention and to completely inform those having ordinary knowledge in the art of the scope of the present invention.

The terminology used herein is for the purpose of describing particular exemplary embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, combustion, plug-in hybrid electric vehicles, hydrogen-powered vehicles and other alternative fuel vehicles (e.g. fuels derived from resources other than petroleum).

It is also understood that the term "solution" as used herein includes dispersions and other fluid admixtures in addition to true solutions.

In an aspect, an electrolyte solution for lithium secondary batteries may be a material constituting an electrolyte applicable to lithium secondary batteries and include a lithium salt, a solvent and a negative-electrode additive. In addition, the electrolyte solution may further include a positive-electrode additive.

The lithium salt may suitably include one or more selected from the group consisting of $LiPF_6$, $LiBF_4$, $LiClO_4$, LiCl, LiBr, LiI, $Li B_{10}Cl_{10}$, $LiCF_3SO_3$, $LiCF_3CO_2$, $LiAsF_6$, $LiSbF_6$, $LiAlCl_4$, $CH_3SO_3Li$, $CF_3SO_3Li$, $LiN(SO_2C_2F_5)_2$, $Li(CF_3SO_2)_2N$, $LiC_4F_9SO_3$, $LiB(C_6H_5)_4$, $Li(SO_2F)_2N$ (LiFSI) and $(CF_3SO_2)_2NLi$.

The lithium salt may be present at a concentration of an amount of about 0.1 to 1.2 M in the electrolyte solution.

The solvent may suitably include one or more selected from the group consisting of carbonate solvents, ester solvents, ether solvents and ketone solvents.

For instance, the carbonate solvent may suitably include dimethyl carbonate (DMC), diethyl carbonate (DEC), dipropyl carbonate (DPC), methylpropyl carbonate (MPC), ethylpropyl carbonate (EPC), ethylmethyl carbonate (EMC), ethylene carbonate (EC), propylene carbonate (PC), butylene carbonate (BC), fluoroethylene carbonate (FEC), vinylene carbonate (VC) or the like. In addition, the carbonate solvent may suibatly include an ester solvent such as γ-butyrolactone (GBL), n-methyl acetate, n-ethyl acetate or n-propyl acetate, or an ether solvent such as dibutyl ether, but is not limited thereto.

In addition, the solvent may further include an aromatic hydrocarbon-based organic solvent. The aromatic hydrocarbon-based organic solvent may include benzene, fluorobenzene, bromobenzene, chlorobenzene, cyclohexylbenzene, isopropylbenzene, n-butylbenzene, octylbenzene, toluene, xylene, mesitylene, and the like, and this solvent may be used alone or in combination.

In addition, $LiPO_2F_2$ may be used as the positive-electrode additive.

For example, allyl(4-nitrophenyl) carbonate represented by the following Formula 1 may be used as the negative-electrode additive added to the electrolyte solution according to the embodiment of the present invention.

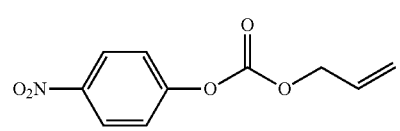

[Formula 1]

The negative-electrode additive may improve the low-resistance characteristics and increase the lifespan by forming a solid electrolyte interphase (SEI) on the negative electrode. The negative-electrode additive be suitably added in an amount of about 3.0% by weight or less, or particularly of about 0.5 to 2.0% by weight, with respect to the total weight of the electrolyte solution.

When the amount of the negative-electrode additive added is greater than about 3.0% by weight, the coating film of the negative electrode may be excessively formed, disadvantageously resulting in high cell resistance and thus decreased cell power. Particularly, when the amount of the negative-electrode additive is less than about 0.5% by weight, the SEI, which is a protective film of the negative electrode, may be insufficiently formed and thus the lifespan of the cell may be greatly reduced. When the amount of the negative-electrode additive is greater than about 2.0% by weight, cell power required for vehicles may decreased.

Meanwhile, the lithium secondary battery includes a positive electrode, a negative electrode and a separator, in addition to the above-described electrolyte solution.

The positive electrode may suitably include an NCM-based positive-electrode active material containing Ni, Co and Mn. In particular, the positive-electrode active material included in the positive electrode in this embodiment preferably contains only an NCM-based positive-electrode active material containing Ni in an amount of about 60% by weight greater based on the total weight of the NCM-based positive electrode active material.

In addition, the negative electrode may suibatly include made of a carbon (C)-based negative-electrode active material alone or include a carbon (C)-based negative-electrode active material.

The carbon (C)-based negative-electrode active material may include at least one material selected from the group consisting of artificial graphite, natural graphite, graphitized carbon fiber, graphitized mesocarbon microbeads, fullerene and amorphous carbon.

Meanwhile, the positive electrode and the negative electrode are produced by mixing each of active materials with a conductive material, a binder and a solvent to prepare an electrode slurry, and then directly coating a current collector with the electrode slurry, followed by drying. In this case, aluminum (Al) may be used as the current collector, but the present invention is not limited thereto. Since such an electrode production method is well known in the art, a detailed description thereof will be omitted.

The binder may facilitate adhesion between particles of each active material or adhesion thereof to the current collector. For example, the binder may suitably include polyvinyl alcohol, carboxymethyl cellulose, hydroxypropyl cellulose, diacetyl cellulose, polyvinyl chloride, carboxylated polyvinylchloride, polyvinylfluoride, an ethylene-oxide-containing polymer, polyvinylpyrrolidone, polyurethane, polytetrafluoroethylene, polyvinylidene fluoride, polyethylene, polypropylene, styrenebutadiene rubber, acrylated styrene butadiene rubber, an epoxy resin, nylon, or the like, but is not limited thereto.

In addition, the conductive material may impart conductivity to the electrode, and any one can be used as long as it is an electrically conductive material that does not cause a chemical change in the battery to be produced, and examples thereof include natural graphite, artificial graphite, carbon black, acetylene black, Ketjen black, carbon fibers, metal powders, such as copper, nickel, aluminum and silver powders, metal fibers and the like. In addition, a conductive material such as a polyphenylene derivative may be used alone or in combination thereof.

The separator prevents a short circuit between the positive electrode and the negative electrode, and provides a passage for lithium ions. Such a separator may suitably include one or more selected from polyolefin-based polymer membranes such as polypropylene, polyethylene, polyethylene/polypropylene, polyethylene/polypropylene/polyethylene and polypropylene/polyethylene/polypropylene, and multiple membranes, microporous films, woven fabrics and nonwoven fabrics thereof. In addition, a porous polyolefin film coated with a resin having excellent stability may be used.

EXAMPLE

Hereinafter, the present invention will be described with reference to Examples and Comparative Examples according to the present invention.

Experiment 1

Experiment of Characteristics Depending on Type of Negative-Electrode Additive

In order to determine various characteristics depending on the type of the negative-electrode additive added to the electrolyte solution, ion conductivity, initial cell resistance, high-temperature durability and high-rate characteristics were measured while changing the type of the negative-electrode additive as shown in Table 1 below, and the result is shown in Table 2 and FIG. 1.

At this time, the lithium salts used to prepare the electrolyte solution were 0.5M $LiPF_6$ and 0.5M LiFSI, and the solvent herein used was a mixture of ethylene carbonate (EC), ethyl methyl carbonate (EMC) and diethyl carbonate (DEC) present at a volume ratio of 25:45:30. In addition, $LiPO_2F_2$ was used as a positive-electrode additive.

NCMN811 was used as the positive electrode and graphite was used as the negative electrode.

At this time, the measurement conditions of ion conductivity, initial cell resistance, high-temperature durability and high-rate characteristics are as follows.

Ion conductivity: measured at room temperature (25° C.)

Initial cell resistance: cell DC-IR measured after formation

High-temperature durability: charging at 0.5 C cc/cv and then discharging at 0.5 C cc, at 2.5 to 4.2 V (cut-off) and at a temperature of 45° C. during each cycle High-rate characteristics: capacity expression value determined while increasing discharge after charging only 0.1 C cc/cv during every cycle

TABLE 1

| Item | Lithium salt (M) | | Solvent (weight ratio) | | | Positive-electrode additive (wt %) | Negative-electrode additive (wt %) | |
|---|---|---|---|---|---|---|---|---|
| | $LiPF_6$ | LiFSI | EC | EMC | DEC | $LiPO_2F_2$ | VC | Additive [Formula 1] |
| Comparative Example | 0.5 | 0.5 | 25 | 45 | 30 | 1 | 2 | — |
| Example 1 | 0.5 | 0.5 | 25 | 45 | 30 | 1 | — | 2 |

TABLE 2

| Item | Ionic conductivity (mS/cm) | Initial cell resistance (%) | High-temperature durability (%) @ 200cyc | High-rate characteristics 2C (%) |
|---|---|---|---|---|
| Comparative Example | 8.19 | 100 | 93.4 | 35.4 |
| Example 1 | 8.24 | 99.4 | 94.7 | 43.9 |

As shown in Table 2 and FIG. 1, when allyl(4-nitrophenyl) carbonate represented by Formula 1 was used as a negative-electrode additive, improvement in ion conductivity, high-temperature durability and high-rate characteristics, was obtained compared to Comparative Example using a conventional general additive VC as a negative-electrode additive under the same conditions. In particular, improved high-rate characteristics along with excellent lifetime in the same content satisfied the performance suitable for vehicle batteries.

Experiment 2

Experiment on High-Rate Characteristics of Negative-Electrode Additive

Figure 2:
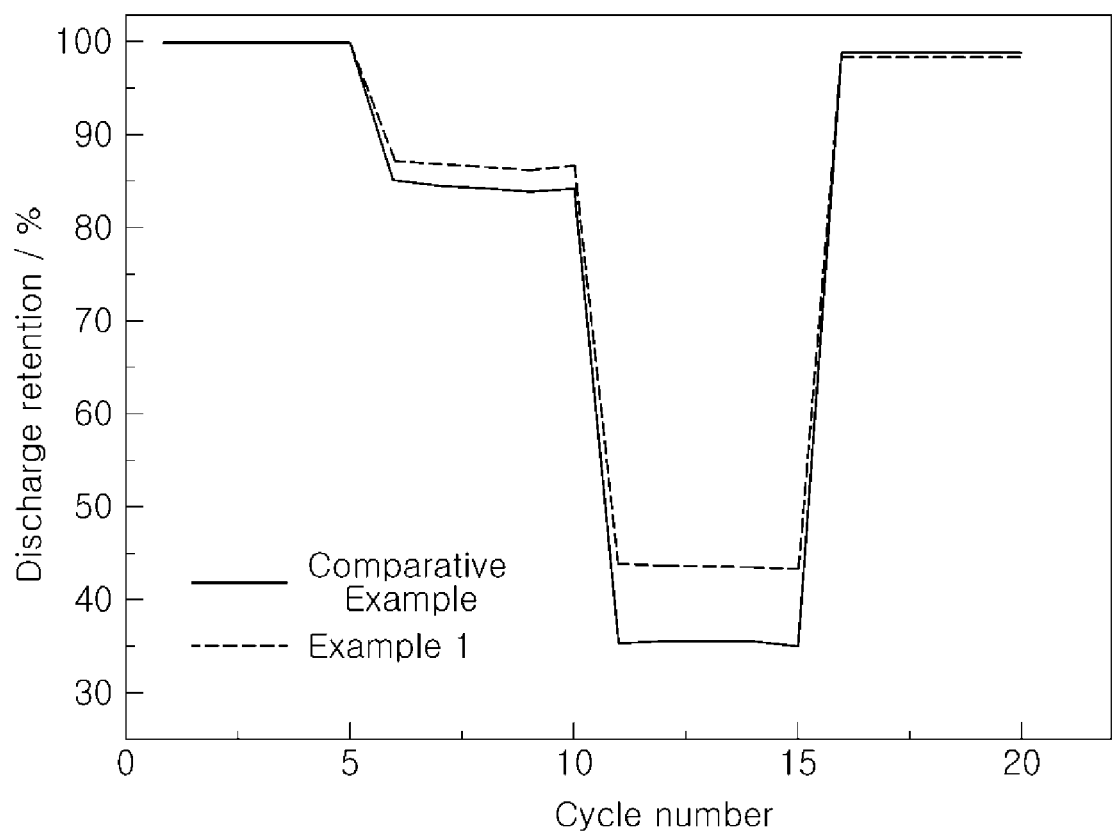
FIG. 2 is a graph showing the evaluation results of characteristics after addition of additives in Experiment 2 according to an exemplary embodiment of the present invention.

Charging and discharging were performed at 0.5 C, 1.0 C, 2.0 C and 0.1 C on Comparative Example and Example 1 of <Experiment 1>, respectively, the corresponding capacity expression values were determined, and the results are shown in FIG. 2.

As shown in FIG. 2, when allyl(4-nitrophenyl) carbonate, represented by Formula 1 was used as a negative-electrode additive exhibits improved high-rate characteristics compared to Comparative Example using a conventional general additive VC as a negative-electrode additive under the same conditions. This means that the improved high-rate characteristics can be based on excellent ion conductivity.

Experiment 3

Figure 3:
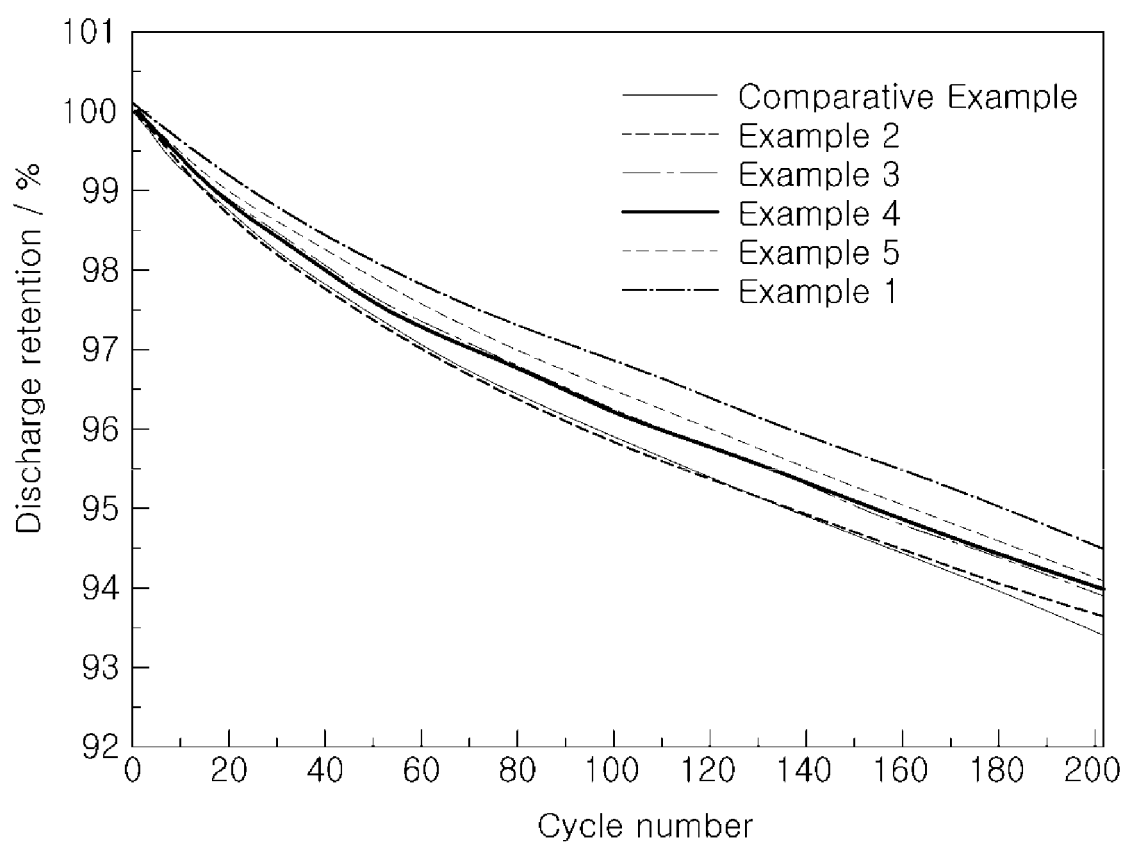
FIG. 3 is a graph showing the evaluation results of characteristics after addition of additives in Experiment 3 according to an exemplary embodiment of the present invention.

Experiment of Characteristics Depending on Content of Negative-Electrode Additive In order to determine various characteristics depending on the type of the negative-electrode additive that is added to the electrolyte solution, ion conductivity, initial cell resistance, high-temperature durability and high-rate characteristics were measured while changing the type of the negative-electrode additive as shown in Table 3 below, and the result is shown in Table 4 and FIG. 3. In this case, other conditions and measurement methods are the same as in <Experiment 1>.

TABLE 3

| Item | Lithium salt (M) | | Solvent (Weight ratio) | | | Positive-electrode additive (wt %) | Negative-electrode additive (wt %) | |
|---|---|---|---|---|---|---|---|---|
| | LiPF$_6$ | LiFSI | EC | EMC | DEC | LiPO$_2$F$_2$ | VC | Additive [Formula 1] |
| Comparative Example | 0.5 | 0.5 | 25 | 45 | 30 | 1 | 2 | — |
| Example 2 | 0.5 | 0.5 | 25 | 45 | 30 | 1 | — | 0.2 |
| Example 3 | 0.5 | 0.5 | 25 | 45 | 30 | 1 | — | 0.5 |
| Example 4 | 0.5 | 0.5 | 25 | 45 | 30 | 1 | — | 1 |
| Example 5 | 0.5 | 0.5 | 25 | 45 | 30 | 1 | — | 1.5 |
| Example 1 | 0.5 | 0.5 | 25 | 45 | 30 | 1 | — | 2 |

TABLE 4

| Item | Ionic conductivity (mS/cm) | Initial cell resistance (%) | High-temperature durability (%) @ 200cyc |
|---|---|---|---|
| Comparative Example | 8.19 | 100 | 93.4 |
| Example 2 | 8.61 | 95.5 | 93.5 |
| Example 3 | 8.52 | 96.1 | 94 |
| Example 4 | 8.39 | 97.5 | 94 |
| Example 5 | 8.28 | 98.4 | 94.1 |
| Example 1 | 8.24 | 99.4 | 94.7 |

As shown in Table 4 and FIG. 2, Examples 1 to 5 including allyl(4-nitrophenyl) carbonate represented by Formula 1 as a negative-electrode additive had improvement ion conductivity and high-temperature durability, compared to Comparative Example using a conventional general additive VC as a negative-electrode additive under the same conditions.

In particular, Example 2, in which the amount of allyl(4-nitrophenyl) carbonate that was added was 0.2% by weight, had similar high-temperature durability to Comparative Example using a conventional general additive VC as a negative-electrode additive under the same conditions. However, the high-temperature durability (e.g., at a temperature of 45° C.) was improved as the amount of the negative-electrode additive added increases.

Therefore, the negative-electrode additive is preferably added in an amount of about 0.5 to 2.0% by weight with respect to the total weight of the electrolyte solution.

According to various exemplary embodiments of the present invention, by adding an additive for forming an SEI film on a negative electrode to an electrolyte solution, the effect of increasing the long-term lifespan of lithium secondary batteries can be expected.

Although the exemplary embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An electrolyte solution for lithium secondary batteries comprising:
   a lithium salt;
   a solvent; and
   a negative-electrode additive,
   wherein the negative-electrode additive comprises allyl (4-nitrophenyl) carbonate represented by the following Formula 1

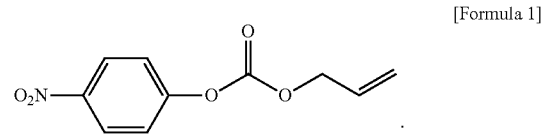 [SMILES: C=CCOC(=O)Oc1ccc([N+](=O)[O-])cc1]

[Formula 1]

2. The electrolyte solution for lithium secondary batteries according to claim 1, wherein the electrolyte solution comprises the negative-electrode additive in an amount of about 3.0% by weight or less with respect to the total weight of the electrolyte solution.

3. The electrolyte solution for lithium secondary batteries according to claim 2, wherein the electrolyte solution comprises the negative-electrode additive in an amount of about 0.5 to 2.0% by weight with respect to the total weight of the electrolyte solution.

4. The electrolyte solution for lithium secondary batteries according to claim 1, wherein the lithium salt comprises one or more selected from the group consisting of LiPF$_6$, LiBF$_4$, LiClO$_4$, LiCl, LiBr, LiI, LiB$_{10}$Cl$_{10}$, LiCF$_3$SO$_3$, LiCF$_3$CO$_2$, LiAsF$_6$, LiSbF$_6$, LiAlCl$_4$, CH$_3$SO$_3$Li, CF$_3$SO$_3$Li, LiN (SO$_2$C$_2$F$_5$)$_2$, Li(CF$_3$SO$_2$)$_2$N, LiC$_4$F$_9$SO$_3$, LiB(C$_6$H$_5$)$_4$, Li(SO$_2$F)$_2$N (LiFSI) and (CF$_3$SO$_2$)$_2$NLi.

5. The electrolyte solution for lithium secondary batteries according to claim 1, wherein the solvent comprises one or more selected from the group consisting of carbonate solvents, ester solvents, ether solvents and ketone solvents.

6. The electrolyte solution for lithium secondary batteries according to claim 1, further comprising a positive-electrode additive,
   wherein the positive-electrode additive comprises LiPO$_2$F$_2$.

7. A lithium secondary battery comprising the electrolyte solution according to claim 1.

8. The lithium secondary battery according to claim 7, further comprising:
   a positive electrode comprising a positive-electrode active material containing Ni, Co and Mn;
   a negative electrode comprising a carbon (C)-based negative-electrode active material; and
   a separator interposed between the positive electrode and the negative electrode.

9. The lithium secondary battery according to claim 7, wherein the lithium secondary battery has a discharge retention of about 94% or greater, measured after 200 cycles, each cycle including 0.5 C cc/cv charging and 0.5 C cc/cv discharging at 2.5 to 4.2V (cut-off) and at temperature of 45° C.

10. A vehicle comprising the lithium secondary battery of claim 7.

\* \* \* \* \*